(12) United States Patent
Nazaroff et al.

(10) Patent No.: US 9,021,646 B2
(45) Date of Patent: May 5, 2015

(54) HIDDEN USER INTERFACE PANEL FOR PERSONAL CARE APPLIANCES AND METHOD OF MAKING SAME

(75) Inventors: Peter George Nazaroff, Seattle, WA (US); Ronald Allan Hagen, Seattle, WA (US); Ahren Karl Johnson, North Bend, WA (US); Raymond Lo, Tai Po (HK)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/995,364

(22) PCT Filed: Dec. 23, 2011

(86) PCT No.: PCT/IB2011/055927
§ 371 (c)(1),
(2), (4) Date: Sep. 26, 2013

(87) PCT Pub. No.: WO2012/090140
PCT Pub. Date: Jul. 5, 2012

(65) Prior Publication Data
US 2014/0007361 A1   Jan. 9, 2014

Related U.S. Application Data

(60) Provisional application No. 61/427,503, filed on Dec. 28, 2010.

(51) Int. Cl.
A61C 17/22   (2006.01)
A61C 17/34   (2006.01)
A46B 15/00   (2006.01)

(52) U.S. Cl.
CPC ............ *A61C 17/225* (2013.01); *A46B 15/0044* (2013.01); *A61C 17/221* (2013.01); *A46B 15/0036* (2013.01); *A61C 17/34* (2013.01)

(58) Field of Classification Search
USPC .................. 15/22.1, 22.2, 28, 167.1; 427/162; 349/62; 362/97.1
See application file for complete search history.

(56) References Cited

U.S. PATENT DOCUMENTS

| | | | |
|---|---|---|---|
| 4,506,956 A | 3/1985 | Dir | |
| 5,477,024 A * | 12/1995 | Share et al. | ............... 219/121.69 |
| 2002/0092104 A1 | 7/2002 | Ferber et al. | |
| 2005/0195614 A1 | 9/2005 | Bayersdorfer | |
| 2007/0188456 A1 | 8/2007 | Shaft et al. | |
| 2010/0024143 A1 | 2/2010 | Dickie | |
| 2010/0061048 A1 | 3/2010 | Mills | |
| 2013/0314900 A1 * | 11/2013 | Timmerman et al. | ........ 362/97.1 |

FOREIGN PATENT DOCUMENTS

EP            1107218 A1 *  6/2001

* cited by examiner

*Primary Examiner* — Shay Karls

(57) ABSTRACT

A power toothbrush appliance (10) which includes a user interface assembly (24) having a hidden interface panel (26) and a method of making same, the appliance including a handle (12, 40) and a brushhead assembly (18) with a brush member (24) for cleaning teeth. The user interface assembly is structured so that when the appliance is in the off condition, the user interface panel is blank, and when the appliance is in an on condition, the indicia associated with the selected operating mode of the toothbrush is illuminated and visible to the user. The interface panel includes a first paint layer of gray or black paint (42) on a translucent handle (40). The mode indicia are etched (44) to the handle in the first paint layer. A second paint layer of white paint (46) is applied over the first layer and is light-transmitting so that when the toothbrush is on, the selected indicia are visible to the user.

14 Claims, 2 Drawing Sheets

HIDDEN USER INTERFACE PANEL FOR PERSONAL CARE APPLIANCES AND METHOD OF MAKING SAME

This invention relates generally to power toothbrushes and other personal care appliances, and more specifically concerns a user interface panel for such appliances.

Typically, power toothbrushes and other personal care appliances will have a user interface panel which provides for user control of, and associated indications of, various operating modes of the appliance. For example, a power toothbrush could have several different cleaning modes involving different brushhead speeds and/or amplitudes, and further could have various sequences of different modes for a set brushing time, e.g. two minutes. A control button or buttons is usually provided for selecting a particular mode, and the panel indication of the selected mode is typically illuminated or otherwise highlighted to provide a clear indication to the user of the mode in which the toothbrush is operating (the selected mode).

Some appliances have a hidden interface panel, also referred to as a dead panel. With such panels, when the appliance is off, the panel is completely blank. When the appliance is on, the panel is visible with the mode indications. This adds to the attractiveness of the appliance. Existing hidden panels, however, are usually complex structurally, requiring a number of different parts, and consequently are more expensive and time consuming to manufacture. These are true hidden panels. Others are more accurately characterized as obscured panels, since the panel indications are still visible to some extent when the appliance is off.

Accordingly, it would be desirable to have a true hidden interface panel in an appliance such as a toothbrush which is relatively simple and inexpensive to manufacture, and requires relatively few additional parts or elements.

Accordingly, disclosed herein is a personal care appliance, and corresponding method of manufacture of an interface panel portion thereof, comprising: an appliance handle; a brushhead assembly which includes a brush member for cleaning teeth; a drive assembly for the brushhead assembly, mounted within the handle and responsive to an on/off switch to produce an oscillating movement of the brushhead assembly; a mode select member; and a user interface assembly on the appliance which includes an interface panel, wherein the user interface assembly is structured so that when the appliance is off, the interface panel is blank, and when the appliance is on, an indicia on the panel corresponding to a selected mode is illuminated and visible to the user, wherein the handle is translucent and includes a plurality of illuminating elements therein, the interface panel including a first layer characterized by blocking light from proceeding therethrough, etched regions corresponding to the mode indicia of the appliance and a second layer covering at least the etched regions, the second layer being illuminated by one or more of the illuminating elements, with the illuminated indicia being is visible to the user.

Figure 1:
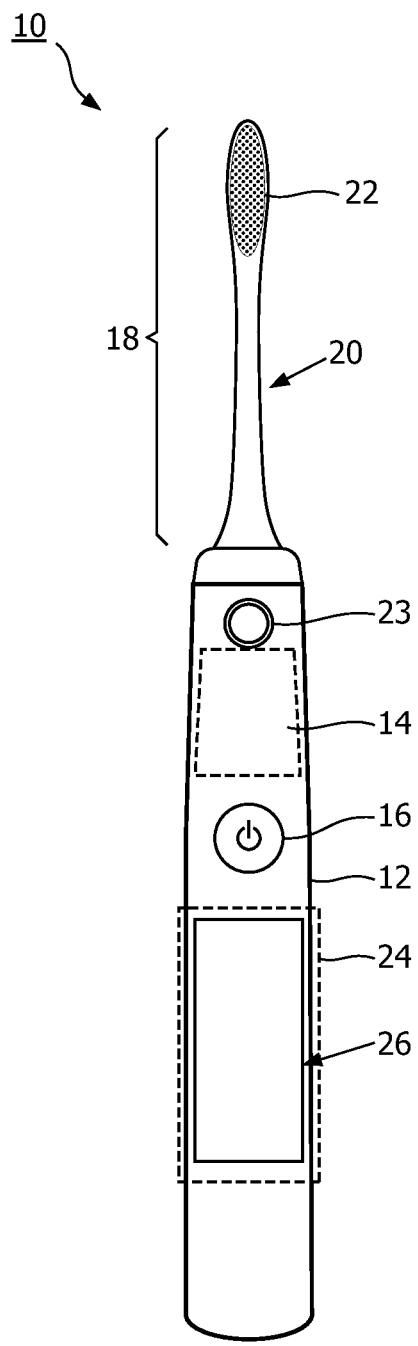
FIG. 1 shows a hidden panel toothbrush wherein the toothbrush is off.
Figure 2:
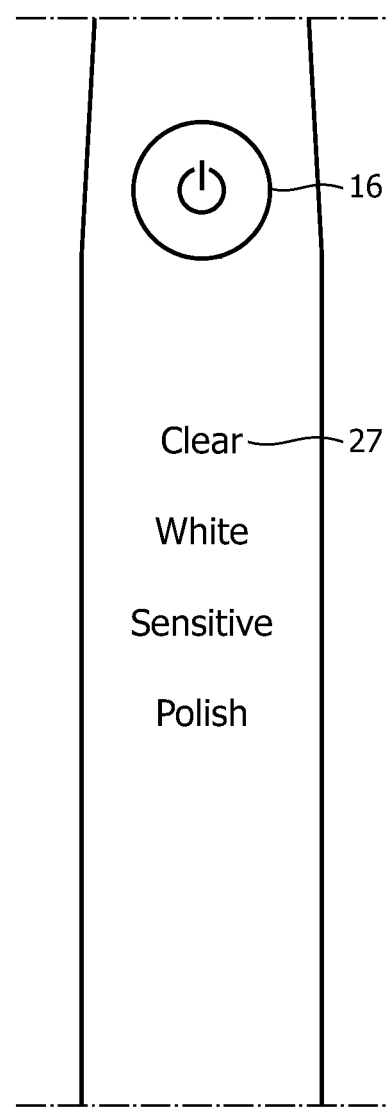
FIG. 2 is an elevational view of the hidden panel portion when the toothbrush is on and one of its operating modes has been selected, with the other available modes being de-selected.

FIG. 1 shows a toothbrush, generally at 10, including a handle portion 12 which in turn includes a drive system 14 therein and an on/off switch 16. Removably secured to handle 12 is a brushhead assembly 18 which typically includes an elongated neck portion 20 and a brush member 22 for cleaning teeth. Located in handle 12 is a user interface assembly 24, which includes a user interface panel 26. In FIG. 1, the user interface panel 26 is hidden or "dead", when the appliance is off, and is illuminated with the particular selected mode of operation, as shown in FIG. 2, when the appliance is on. The interface assembly will include a mode select button or switch element 23.

Figure 4:
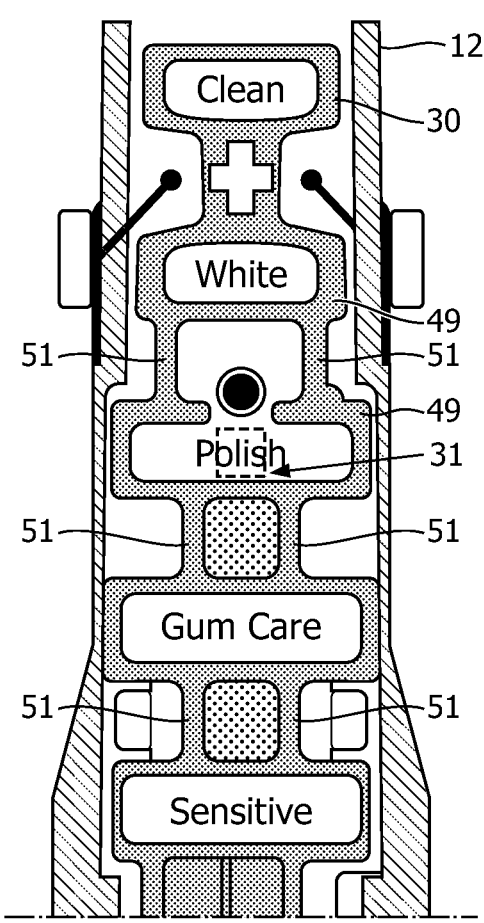
FIG. 4 is a top view showing a baffle structure around illumination elements for the handle having several different possible modes.
Figure 5:
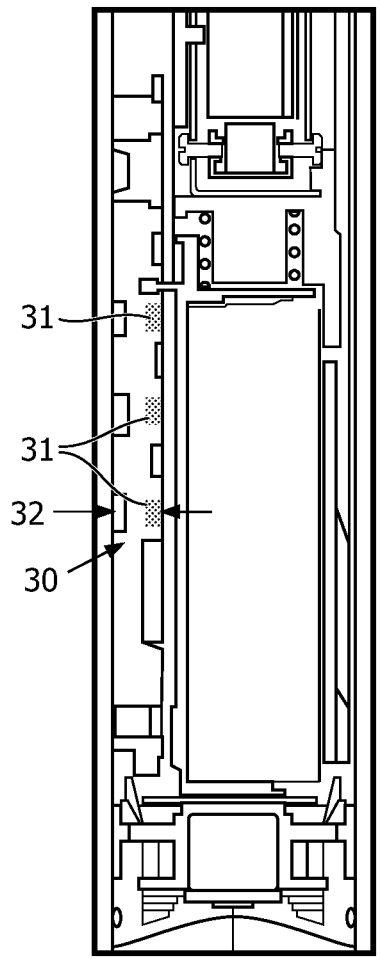
FIG. 5 is a cross-section showing the position of LED lights and the baffle structure of FIG. 4.

The user interface assembly and the interface panel can take various arrangements. For a toothbrush, the interface assembly and the panel will have use indications representing a series of cleaning modes or other oral care modes, usually characterized by particular combinations of frequency and amplitude of the brush member action. The individual indications or indicia can be in the form of words or symbols or both. In FIG. 2, the panel 26 is brightly illuminated with the selected mode "clean", referred to at 27, while the other modes "white", "sensitive" and "polish", being de-selected, are less illuminated. This is only one example of a hidden panel. Other words/symbols can be used, for a wide variety of modes/operations of the toothbrush. Another panel example is shown in FIG. 4. The panel indicia are illuminated by separate LEDs 31, which are bright enough to illuminate the words for the user. One LED is illustrated in FIG. 4 for example, for the mode "polish". The individual LEDs are separated by a baffle arrangement 30 which surrounds each of the LEDs, confining the light produced by each LED to its associated front panel indicia. This baffle arrangement is illustrated in FIG. 4. The baffle assembly 30 is plastic and is positioned so that a front surface thereof abuts the internal surface 32 of the handle, as illustrated in FIG. 5, which shows the internal structure of the handle, including the LEDs, which are positioned about 5 mm from the inner surface of the handle and their surrounding baffle structure. This structure is described in more detail in the following paragraphs.

Figure 3:
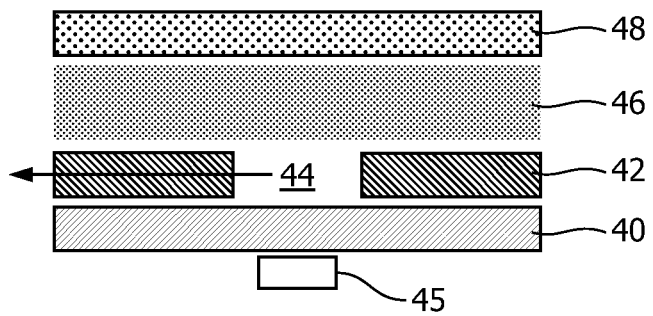
FIG. 3 is a diagram showing a cross-section of the hidden panel.

FIG. 3 shows a cross-section of the user interface assembly/hidden panel and illustrates not only the final hidden panel, but also the particular process of manufacturing the user interface/hidden panel.

Referring to FIG. 3, the handle 40 in the region of the user interface panel 30 is translucent, i.e. it permits light from LEDs positioned internally of the handle to shine therethrough. In one embodiment, the handle is plastic, approximately 2.2 mm thick.

In a first step, a first layer of paint 42 is applied, typically gray or black. The color must be such as to block light from the LEDs or other illumination sources in the handle. This first paint layer in the embodiment shown is 13 µm±3 µm and is referred to as a masking layer.

In a second step, the desired mode indicia for the panel are etched in the first paint layer 42. Typically, this is done by a laser, although other means could be used. The etching extends down to the surface of the handle 40, so that light can proceed through the etched area 44 in FIG. 3, from a source LED 45. The LEDs can be various colors but typically will be white. Examples of mode indicia are shown in FIGS. 2 and 4.

In the next (third) step, a second paint layer 46 is applied over at least the areas that have been etched. In the embodiment shown, the second paint layer is white, so that the illuminated mode indicia appear white. In the embodiment shown, layer 46 is approximately 25 µm±5 µm thick. Typically, layer 46 is a single layer, although multiple layers could be used. Paint layer 46 should not contain any pigment which would otherwise block at least some of the light from going through. It is desirable that the illumination be bright enough that the indicia are readily visible. White paint is preferred, as indicated above, but other light colors, such as light pink, yellow or even silver could be used.

On top of second paint layer 46, a clear coat layer 48 of polyurethane or similar material is applied. Layer 4-8 protects the panel from wear.

In summary, the panel includes a base layer of light-blocking paint, which is etched with the desired mode indicia, a second layer of paint which provides the desired color for the indicia, and a final protective coat.

The user interface panel 26, which can be located anywhere on the toothbrush, is shown in the handle in FIG. 1 for illustration, on which a plurality of different operating mode indicia can be provided. The illumination for the panel is supplied by a plurality of LEDs 31 positioned within the handle and spaced approximately less than 5 mm or so from the interior surface of the handle. Typically, there will be one LED per mode indicia. The LEDs will typically be white, but could also be other colors. The user interface assembly also includes a baffle arrangement 30 which confines light from each LED, respectively, to the area surrounding the associated mode indicia which it illuminates. The baffle arrangement, usually of plastic, prevents light from one LED spilling over and at least partially illuminating a neighboring mode indicia. The baffle arrangement 30 is a few millimeters high and has a configuration shown in FIG. 4, with individual baffle sections 49 encircling their associated LEDs and each section 49 being connected to adjacent sections by connecting portions 51. In the embodiment shown, there is a minimum 0.3 mm clearance in the vertical direction and 0.28 mm clearance in the horizontal direction between each baffle section in the baffle arrangement 30 and their associated etched indicia.

In operation, when the toothbrush is off, all the LEDs in the handle are off and the hidden panel is completely blank, with nothing visible. When the toothbrush is on, the selected mode in which the toothbrush is actually operating is brightly illuminated, with the other modes (de-selected) being either not illuminated at all or illuminated at a low level. In the latter arrangement, the user has the opportunity to see all of the modes available, with the selected mode being readily visible by a higher level of illumination than the other indicia. In such a case, the LEDs have two operating levels of illumination.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A personal care appliance, comprising:
an appliance handle;
a brushhead assembly which includes a brush member for cleaning teeth;
a drive assembly for the brushhead assembly, mounted within the handle and responsive to an on/off switch to produce an oscillating movement of the brushhead assembly, wherein the drive assembly is capable of producing a plurality of modes of operation of the brushhead assembly;
a mode select member; and
a user interface assembly on the appliance which includes an interface panel, wherein the user interface assembly is structured so that when the appliance is off, the interface panel is blank, and when the appliance is on, an indicia on the panel corresponding to a selected mode of operation is illuminated and visible to the user, wherein the handle is translucent and includes a plurality of illuminating elements positioned within the handle, the interface panel including a first layer of light-blocking paint on the outer surface of the handle, etched regions extending through the first layer defining the indicia representing the plurality of modes of operation of the appliance, and a second layer of light-illuminating paint on the outer surface of the handle covering at least the etched regions, the second layer being illuminated by one or more of the illuminating elements, with the illuminated indicia being visible to the user, and wherein the second layer provides a generally even outside surface.

2. The appliance of claim 1, wherein the illuminating elements are LEDs, one for each indicia.

3. The appliance of claim 2, wherein the LEDs are white LEDs.

4. The appliance of claim 1, including a third layer which is clear, providing protection for the interface panel.

5. The appliance of claim 1, wherein handle is plastic.

6. The appliance of claim 1, wherein the first layer is a gray or black paint and wherein the second layer is a white paint.

7. The appliance of claim 2, wherein the LEDs have two levels of brightness, one level to illuminate a selected indicia and another lower level to illuminate non-selected indicia.

8. The appliance of claim 2, including a baffle structure around the LEDs which substantially confine the light of each LED to its associated indicia.

9. A method for making a hidden panel assembly for use in a power toothbrush or other personal care appliance having a brushhead assembly which includes a brush member for cleaning teeth, a drive assembly for the brushhead assembly, mounted within the handle and responsive to an on/off switch to produce an oscillating movement of the brushhead assembly, and a translucent handle and a plurality of light sources positioned within the handle, the method comprising the steps of:
applying a first layer of light-blocking paint to the outer surface of the handle in a hidden panel region thereof;
etching the first layer down to the handle, the etching representing operating modes of the appliance; and
applying a second layer of light-transmitting paint to the outer surface of the handle, on top of the etched regions, wherein when the appliance is on, selected indicia are illuminated through the second layer, visible to the user, and when the appliance is off, the handle is blank, without any indicia being visible to the user, and wherein the second layer provides a generally even outside surface.

10. The method of claim 9, wherein the first layer is a gray or black paint.

11. The method of claim 9, wherein the second layer is a white paint.

12. The method of claim 9, including the further step of providing baffle means around each light source to confine illumination for each light source to its associated indicia.

13. The method of claim 9, wherein the light sources are individual LEDs.

14. The method of claim 9, including the further step of applying a clear protective layer on top of the second layer.

* * * * *